United States Patent [19]

Palladino et al.

[11] 4,232,013
[45] Nov. 4, 1980

[54] 16,17-PYRAZOLINO- AND 16,17-ISOPYRAZOLINO-1,4-PREGNADIENE DERIVATIVES

[75] Inventors: Gaetano Palladino; Mario Micciarelli, both of Milan, Italy

[73] Assignee: Lark S.p.A., Milan, Italy

[21] Appl. No.: 965,058

[22] Filed: Nov. 30, 1978

[30] Foreign Application Priority Data

Dec. 3, 1977 [GB] United Kingdom ............... 50464/77

[51] Int. Cl.³ .................... A61K 31/58; C07J 43/00
[52] U.S. Cl. ................... 424/241; 260/239.5; 260/397.45
[58] Field of Search ............. 260/239.5; 424/241; /Machine Searched Steroids

[56] References Cited

U.S. PATENT DOCUMENTS 3,350,394   10/1967   Agnello et al. .............. 260/239.5
3,384,637   5/1968    Diassi .......................... 260/239.5
3,538,130   11/1970   Hewett et al. ................ 260/397.45

OTHER PUBLICATIONS

Taub et al., Journ. Oreg. Chem. 29 (1964) pp. 3486–3495.

Primary Examiner—Elbert L. Roberts
Attorney, Agent, or Firm—Stevens, Davis, Miller & Mosher

[57] ABSTRACT

New 16,17-pyrazolino- and 16,17-isopyrazolino-1,4-pregnadiene-derivatives have been prepared, useful as antiinflammatory agents on topical and/or systemic administration. An analogy process for the preparation of 16,17-pyrazolino-1,4-pregnadiene derivatives and the quite surprising conversion of the latter ones to 16,17-isopyrazolino-1,4-pregnadiene derivatives are also disclosed. The results of pharmacological comparative trails of some new products of the present invention v. fluocinolone acetonide are reported.

13 Claims, No Drawings

16,17-PYRAZOLINO- AND 16,17-ISOPYRAZOLINO-1,4-PREGNADIENE DERIVATIVES

BACKGROUND OF THE INVENTION

The 16α,17α-pyrazolino-pregnane-derivatives characterized by the grouping

in the 16,17-position of the steroid skeleton are widely described in the literature. However said derivatives are limited to steroids of the $\Delta^5$-pregnene- or to the $\Delta^4$-pregnene series, such as derivatives of pregnelone, progesterone, hydrocortisone and the like. See, for instance, British Pat. No. 901.092 (application date 22.7.1957), U.S. Pat. No. 3,359,287 (application date 16.11.1959), U.S. Pat. No. 3,350,394 (application date 26.4.1961), U.S. Pat. No. 3,086,029 (application date 12.1.1962), Brit. Pat. Nos. 923,623 and 923,624 (application date 1.10.1958). To our best knowledge there is only one example of a $\Delta^{1,4}$-pregnadiene-derivative bearing a 16α,17α-pyrazolino-group, namely 9α-fluoro-16α,17α-methyleneazo-$\Delta^{1,4}$-pregnadiene-11β 21-diol-3,20-dione 21-acetate, reported in the literature (J.Org.-Chem., 29, 3486–95, 1964). However in all the above reported patents and publication, the 16α,17α-pyrazolino-derivatives have been described or reported as mere intermediates for the preparation of 16β-methyl-, $\Delta^{16}$-16-methyl-, 16α,17α-methylene- and 16-methylene-17α-hydroxy-derivatives. Neither direct nor indirect indications have been made in the literature that the 16α,17α-pyrazolino-derivatives show pharmacological and therapeutic activities.

DETAILED DESCRIPTION OF THE INVENTION

The present invention relates to a new class of anti-inflammatory steroids and to the preparation thereof. It is an object of this invention to provide new steroid derivatives of the pregnane series which possess valuable pharmacological properties, particularly anti-inflammatory and anti-rheumatoid arthritic activity with practical absence of side-effects such as sodium retention, adrenal inhibition, thymolytic activity and the like present in certain known physiologically active steroids. The new compounds of the present invention may be administered by topical, by interarticular, and by systemic route.

The new compounds of the present invention are 16α,17α-pyrazolino-$\Delta^{1,4}$-pregnadiene derivatives of the following 2 general formulae I and II

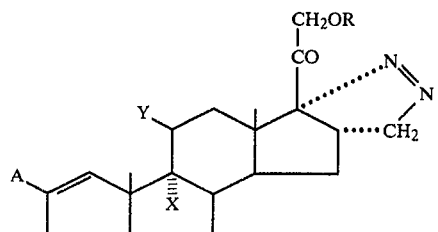

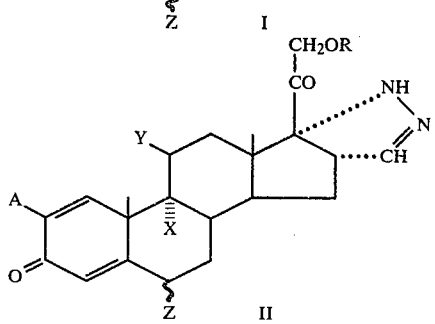

in which
A may be a hydrogen or a bromine or chlorine atom;
X may be a hydrogen, or a fluorine or chlorine atom;
Y may be a β-hydroxyl, or a keto-group or a chlorine atom;
Z may be a hydrogen, or an α- or β-fluorine atom or an α-methyl-group;
R may be hydrogen or an acyl residue selected from the group consisting of a mono- or dicarboxyl organic acid having from 2 to 8 carbon atoms, of methasulfobenzoic acid and of phosphoric acid.

It is a further object of the present invention to provide pharmaceutical compositions for use in the topical, intraarticular and systemic treatment of a wide range of inflammatory disorders, rheumatoid arthritis, allergic diseases and the like, which comprises incorporating an effective amount of compounds of formulae I and/or II together with a suitable carrier for said steroid.

The compounds of formula I can be prepared from a 1,4,16-pregnatriene derivative of the general structural formula III:

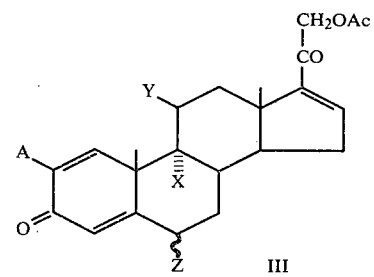

wherein Ac indicates an acetyl-group, and A, X, Y, and Z have the same meaning as heretofore reported for formulae I and II. 1,4,16-Pregnatriene derivative is thus reacted with diazomethane according to general methods known from the literature involving a $\Delta^{16}$-pregnene-substrate, for instance see British Pat. No. 901,092 (application date 22.7.1957). The compounds of formula II can be prepared from the compounds of formula I by reaction of the latter ones with a strong mineral acid such as hydrochloric acid, hydrobromic acid, hydrofluoric acid, perchloric acid and the like. The concentration of said acids, the temperature, and duration of the reaction are not critical, but it is preferred to operate with aqueous concentrate acids, in the cold and for a short period of time.

This conversion is a quite surprising result, as it is well known from the literature (U.S. Pat. No. 3,086,029, column 2 and 8, lines 39–48) that by reaction of 16(17)-diazomethane adduct with a strong acid a $16\alpha,17\alpha$-methylene-pregnane derivative is obtained.

The compounds of structure II do indeed represent one of the most surprising aspect of the present invention.

In fact their structure, the simple and smooth process for preparing them, as well as their unexpected useful pharmacological activity are—so to say—the three points confirming the great interest of the present invention. As far as their structure is concerned, there exists only one example in the literature (U.S. Pat. No. 3,359,287 column 1) in which an 'isomer' structure

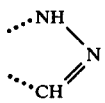

is attributed to the so-called "diazomethane adduct II", instead of the more likely one

However in the same U.S. Pat. No. 3,359,287, column 3, lines 4–10 there is quoted the following sentence, which "weakens the firm statement of the structure reported for compound II in column 1": ". . . For convenience in structural representation, the double bond in the adduct portion of the molecule is represented as being between a carbon and a nitrogen atom. However the double bond may be elsewhere in the ring and it is to be understood that II is intended to represent the reaction product of a pregnadienolone (I) and diazomethane . . . ". This sentence makes the actual structure indeterminate and vague.

We succeeded to ascertain unequivocally the structures of both compounds of formula I and II by means of an accurate investigation with mass spectrography, infra-red spectrophotometry and nuclear magnetic resonance.

Compounds of formula II are moreover characterized by physico-chemical parameters quite different from those of compounds of formula I, especially as far as specific rotatory power and the $E_1{}_{cm}{}^{1\%}$ at UV. spectrophotometry are concerned.

In fact the rotatory power values are 6 times higher, and the $E_1{}_{cm}{}^{1\%}$-values are 10% higher than the corresponding values of compounds of formula I.

In particular the structure of compounds II was confirmed by means of:

mass spectrography, which gave a molecular weight identical to that of compounds of structure I;
infra-red spectrophotometry, which showed the disappearance of the peak at 1,540 cm$^{-1}$, characteristic of the double bond —N=N—;
N.M.R., which showed a singulet at 7,90$\delta$ due to double bond —CH=N—.

Moreover we have found that the conversion Compound I→Compound II is an irreversible process, the thermodynamic equilibrium being completely shifted towards Compound II, which represents the form with the lowest level of free energy.

In order to distinguish compound I from compound II by chemical name, we have tentatively called the former one as: '$16\alpha,17\alpha$-pyrazolino-1,4-pregnadiene-derivative' and the latter one as: '$16\alpha,17\alpha$-isopyrazolino-1,4-pregnadiene-derivative'. The Compound II of the present invention, in which R is an acyl residue *different from acetyl,* and it is selected from the group consisting of a mono- or dicarboxyl organic acid having from 3 to 8 carbon atoms, of methasulfobenzoic acid and of phosphoric acid, may be prepared by starting from Compound II in which R is the acetyl residue according to an analogy process as hereinbelow explained. The analogy process consists essentially in a suitable alkaline hydrolysis of Compound II in which R is the acetyl residue under nitrogen atmosphere to give the corresponding 21-alcohol, and then in a suitable acylation of said 21-alcohol to give the desired 21-ester. The details are given in Examples from 7 to 16.

The following EXAMPLES illustrate methods of carrying out the present invention but it is to be understood that these examples are given for the purpose of illustration and not of limitation.

EXAMPLE 1

$16\alpha,17\alpha$-Pyrazolino-1,4-pregnadiene-$9\alpha$-fluoro-$11\beta$,21-diol-3,20-dione-21-acetate (compound I in which X=F, Y=OH, Z=H, A=H, R=—CO—CH$_3$)—Laboratory code Pyr—F—AC)

To a two phase solution of 53 ml of aqueous 40% potassium hydroxide and 240 ml of ethyl ether, 17,7 g of nitroso-methylurea were slowly added with stirring and cooling in an ice bath.

To the resulting ether solution of diazomethane 3 g of $9\alpha$-fluoro-1,4,16-pregnatriene-$11\beta$,21-diol-3,20-dione 21-acetate (compound III, in which X=F, Y=OH, Z=H, A=H) dissolved in 50 ml of methylene chloride were added with stirring and the temperature was kept at 10°–15° C.

The reaction mixture was maintained at this temperature for one hour and the excess of diazomethane was decomposed with acetic acid at 0° C.

The solution was washed with water, dried over anhydrous sodium sulfate, filtered and then concentrated "in vacuo" to dryness.

The residue was triturated with 20 ml of isopropyl ether, filtered and dried to give 2.8 g of the desired compound I,
M.p. 195° C.
UV. Spectrum: λmax.=230 mμ; $E_1{}_{cm}{}^{1\%}$=367.7.
[α]=+63° (c=1%, dioxane).
IR. Spectrum (nujol): 3315-1760-1730-1660-1615-1605-1540 cm$^1$.

EXAMPLE 2

$16\alpha,17\alpha$-Isopyrazolino-1,4-pregnadiene-$9\alpha$-fluoro-$11\beta$,21-diol-3,20-dione-21-acetate (Compound II in which X=F, Y=OH, A=Z=H, R=—CO—CH$_3$; laboratory code 16-17 MF-AC)

To 15 ml of 36% aqueous hydrochloric acid cooled to 0° C., 2.8 g of the compound I obtained as described in Example 1, were added with stirring. The reaction mixture was kept at 0° under stirring for a further 15 min., then it was poured in 150 ml of water and crushed ice. The precipitate thus formed, was filtered, washed with water, and dried.

Yield: 2.5 g of crude Compound II.

Upon crystallization from chloroform-methanol 2 g of pure compound II were obtained showing the following characteristics:

m.p. 225° C.; $[\alpha]_D = +311$ (c=1%, dioxane);
UV. Spectrum: λmax.=238 mμ; $E_{1\ cm}^{1\%}=414$.
IR. Spectrum (nujol): 3530-3300-1735-1705-1665-1620-1605 cm$^{-1}$.

EXAMPLE 3

16α,17α-Pyrazolino-1,4-pregnadiene-6α,9α-difluoro-11β,21-diol-3,20-dione 21-acetate (Compound I in which X=F, Y=OH, Z=αF, R=COCH₃, A=H; laboratory code Pyr.Dif-AC)

By starting from 6α,9α-difluoro-1,4,16-pregnatriene-11β,21-diol-3,20-dione-21-acetate (compound III, X=F, Y=OH, Z=αF, A=H) and by operating according to the method illustrated in Example 1, the above compound I was obtained, showing the following characteristics:

m.p. 198° C.; $[\alpha]_D = +56.6°$ (c=1%, dioxane);
UV. Spectrum: λmax=238 mμ; $E_{1\ cm}^{1\%}=376.16$.
IR. Spectrum (nujol): 3500-1740-1725-1665-1630-1605-1550 cm$^{-1}$.

EXAMPLE 4

16α,17α-Isopyrazolino-1,4-pregnadiene-6α,9α-difluoro-11β,21-diol-3,20-dione 21-acetate (compound II: X=F, Y=OH, Z=αF, A=H, R= —COCH₃; laboratory code 16-17 M Dif-AC)

By starting from 16α,17α-pyrazolino,1,4-pregnadiene-6α,9α-difluoro-11β,21-diol-3,20-dione 21-acetate (prepared according to Example 3) and by operating according to the method illustrated in Example 2, the title compound II was prepared, showing the following characteristics:

m.p. 224.5° C.; $[\alpha]_D=309.5°$ C. (c=1%, dioxane);
UV. Spectrum: λmax.=238 mμ; $E_{1\ cm}^{1\%}=416$.
IR. Spectrum (nujol): 3580-3280-1735-1725-1670-1620-1605 cm$^{-1}$.

EXAMPLE 5

16α,17α-Pyrazolino-1,4-pregnadiene-11β,21-diol-3,20-dione 21-acetate (compound I: A=X=Z=H, R=COCH₃; laboratory code Pyr-T₁)

By starting from 1,4,16-pregnatriene-11β,21-diol-3,20-dione 21-acetate (compound III: A=X=Z=H, R=COCH₃) and by operating according to the method illustrated in Example 1., the title compound I was prepared, showing the following characteristics:

IR. Spectrum (nujol): 3400-1740-1725-1655-1620-1600-1550 cm$^{-1}$.

EXAMPLE 6

16α,17α-Isopyrazolino-1,4-pregnadiene-11β,21-diol-3,20-dione 21-acetate (compound II: A=X=Z=H, R=COCH₃; laboratory code 16-17 MT₁)

By starting from the Compound I prepared in the previous Example and by operating according to the method illustrated in Example 2, the title compound II was obtained.

EXAMPLE 7

16α,17α-Isopyrazolino-1,4-pregnadiene-9α-fluoro-11β,21-diol-3,20-dione (compound II in which X=F, Y=OH, A=Z=H, R=—H; laboratory code 16-17 MF)

To a suspension of 10 g of 16α,17α-isopyrazolino-1,4-pregnadiene-9α-fluoro-11β,21-diol-3,20-dione-21-acetate (prepared according to Example 2) in 200 ml of methanol kept at 0°±2° C. under continuous bubbling of nitrogen and with stirring a solution of 2 g of sodium bicarbonate in 20 ml of water was added. Stirring was continued for a further 45 minutes. The reaction mixture was neutralized with acetic acid and then the methanol was distilled off "in vacuo". The resulting suspension was cooled to 0° C. and filtered, the crude product was washed with water and dried "in vacuo".

Yield 7,1 of 16α,17α-isopyrazolino-1,4-pregnadiene-9α-fluoro-11β,21-diol-3,20-dione.

EXAMPLE 8

16α,17α-Isopyrazolino-1,4-pregnadiene-6α,9α-difluoro-11β,21-diol-3,20-dione (Compound II: X=F, Y=OH, Z=F, A=H, E=—H; laboratory code 16-17 M Dif)

By starting from 16α,17α-isopyrazolino-1,4-pregnadiene-6α,9α-difluoro-11β,21-diol-3,20-dione 21-acetate (prepared according to Example 4) and by operating according to the method illustrated in Example 7, the title compound II was prepared.

EXAMPLE 9

16α,17α-Isopyrazolino-1,4-pregnadiene-9α-fluoro-11β,21-diol-3,20-dione-21-propionate (compound II in which X=F, Y=OH, A=Z=H, R=—CO—CH₂₅; laboratory code 16-17 MF-Pr)

To a solution of 2 g of 16α,17α-isopyrazolino-1,4-pregnadiene-9α-fluoro-11β,21-diol-3,20-dione (prepared according to Example 7) in 30 ml of anhydrous pyridine at room temperature a mixture of 1 ml of propionic anhydride and 10 ml of anhydrous tetrahydrofuran was added dropwise over a period of 30 minutes with stirring.

The reaction mixture was kept for a further three hours, then it was poured into a separatory funnel containing 300 ml of icy distilled water and 10 ml of concentrated sulfuric acid. The mixture was thoroughly shaken 3 times with 50 ml of methylisobutylketone each time.

The combined organic layer was shaken with a saturate aqueous solution of sodium bicarbonate and with water, then it was dried over anhydrous magnesium sulfate. The solution was concentrated "in vacuo" to a volume of about 10 ml. The residue was taken up with 50 ml of isopropyl ether and kept at 0° C. for three hours. The precipitate thus formed was filtered and washed with isopropyl ether. The crude product was recrystallized from acetone-hexane.

Yield 1,5 g of the title compound showing the following characteristics:

IR. Spectrum (nujol): 3570-3350-3290-1740-1725-1670-1620-1605 cm$^{-1}$.

EXAMPLE 10

16α,17α-Isopyrazolino-1,4-pregnadiene-9α-fluoro-11β,21-diol-3,20-dione-21-butyrate (laboratory code 16–17 MF Bu)

To a suspension of 2 g of 16α,17α-isopyrazolino-1,4-pregnadiene-9α-fluoro-11β,21diol-3,20-dione (prepared according to Example 7) in 20 ml of anhydrous pyridine at room temperature a mixture of 1,2 ml of butyrric anhydride and 12 ml of anhydrous tetrahydrofuran was added dropwise over a period of 20 minutes with stirring.

The reaction mixture was kept for a further 4 hours, at room temperature then it was poured into a flask containing 200 ml of icy distilled water and 7 ml of concentrated sulfuric acid. The solid thus separated was filtered, washed with water and dried "in vacuo" to constant weight. The crude product (2,1) was dissolved in 20 ml of acetone, decoulorized with 50 mg of charcoal DARCO G 60.

After filtration the solution was concentrated, then 45 ml of hexane were added and kept at 0° C. overnight.

The crystalline product was filtered and dried. Yield 1,3 g of the title compound showing the following characteristics:

IR. Spectrum (nujol): 3370-3295-1740 (s)-1725-1670-1620-1605 cm$^{-1}$.

EXAMPLE 11

16α,17α-Isopyrazolino-1,4-pregnadiene-9α-fluoro-11β,21-diol-3,20-dione-21-valerate (laboratory code 16–17 MF-Va)

In a flask there were poured 20 ml of anhydrous pyridine, 2 g of 16α,17α-Isopyrazolino-1,4-pregnadiene-9α-fluoro-11β,21-diol-3,20-dione (prepared according to Example 7) and 4 ml of valeric acid anhydride.

The reaction mixture was kept for a further 3 hours at room temperature, then it was poured into a separatory funnel containing 200 ml of icy distilled water and 7 ml of concentrated sulfuric acid. The mixture was thoroughly shaken 4 times with 50 ml of methylene chloride each time. The combined organic layer was shaken with a saturate aqueous solution of sodium bicarbonate and with water, then it was dried over anhydrous sodium sulfate. The solution was concentrated "in vacuo" to an oily residue, which was chromatographed over a column containing 150 g of Florisil. The column was then eluted with methylene chloride/acetone 9:1.

The eluates were concentrated "in vacuo" to dryness. The residue was recrystallized from isopropyl ether/methylene chloride.

Yield 1,3 of the title compound showing the following characteristics:

IR. Spectrum: 3600-3315 (s)-3295-1750-1730-1720-1665-1620-1605 cm$^{-1}$.

EXAMPLE 12

16α,17α-Isopyrazolino-1,4-pregnadiene-9α-fluoro-11β,21-diol-3,20-dione-21-benzoate (laboratory code 16–17 MF-Bz)

To a solution of 2 g of 16α,17α-isopyrazolino-1,4-pregnadiene-9α-fluoro-11β,21-diol-3,20-dione (prepared according to Example 7) in 30 ml of anhydrous pyridine cooled to −10° C. a mixture of 1,2 ml of benzoyl chloride and of 12 ml of tetrahydrofuran was added dropwise over a period of 30 minutes with stirring. The reaction mixture was kept for a further two hours at −5° C., then it was poured into 300 ml of ice/water and 12 ml of concentrated sulfuric acid.

The solid thus separated was filtered, washed with water and dried "in vacuo" to constant weight.

The crude product was chromatographed over a column containing 150 g of Florisil, then eluted with methylene chloride/ethyl ether 96/4. The eluates were concentrated "in vacuo" to dryness. The residue was recrystallized from acetone/ethylether.

Yield 1,15 g of the title compound showing the following characteristics:

IR. Spectrum (nujol): 3560-3330-1730-1710-1620-1615-1605-725 cm$^{-1}$.

EXAMPLE 13

16α,17α-Isopyrazolino-1,4-pregnadiene-6α,9α-difluoro-11β,21-diol-3,20-dione-21-butyrate (laboratory code 16–17 M Dif-Bu)

By starting from 16α,17α-isopyrazolino-1,4-pregnadiene-6α,9α-difluoro-11β,21-diol-3,20-dione (prepared according to Example 8) and by operating according to the method illustrated in Example 10, the title compound was prepared, showing the following characteristics:

IR. Spectrum (nujol): 3370-3320-1750-1720-1665-1620 (s)-1610 cm$^{-1}$.

EXAMPLE 14

16α,17α-Isopyrazolino-1,4-pregnadiene-6α,9α-difluoro-11β,21-diol-3,20-dione-21-valerate (laboratory code 16–17 M Dif-Va)

By starting from 16α,17α-isopyrazolino-1,4-pregnadiene-6α,9α-difluoro-11β,21-diol-3,20-dione (prepared according to Example 8) and by operating according to the method illustrated in Example 11, the title compound was prepared, showing the following characteristics:

IR. Spectrum (nujol): 3335-3300-1750-1720-1665-1620 (s)-1615 cm$^{-1}$.

EXAMPLE 15

16α,17α-Isopyrazolino-1,4-pregnadiene-6α,9α-difluoro-11β,21-diol-3,20-dione-21-pivalate (laborabory code 16,17 M Dif-Piv)

By starting from 16α,17α-isopyrazolino-1,4-pregnadiene-6α,9α-difluoro-11β,21-diol-3,20-dione (prepared according to Example 8), by using pivaloyl chloride as acylating agent, and by operating as indicated in the previous Examples, the title compound was prepared showing the following characteristics:

IR. Spectrum (nujol): 3660-3570-3350 (s)-3295-1740-1725-1670-1640-1605.

EXAMPLE 16

16α,17α-Isopyrazolino-1,4-pregnadiene-9α-fluoro-11β,21-diol-3,20-dione-21-succinic acid ester (laboratory code 16–17 MF-HS)

By starting from 16α,17α-isopyrazolino-1,4-pregnadiene-9α-fluoro-11β,21-diol-3,20-dione (prepared according to Example 7), by using succinic anhydride as acylating agent, and by operating as indicated in the previous Examples, the title compound was prepared.

Biological assays

The topical anti-inflammatory activity of the new compounds of this invention was determined using the cotton granuloma assay. This test was performed according to C. A. Winter and C. C. Porter J. Am. Pharm. Ass. Sci., Ed. 46, 515. 1957 using adult female albino rats (Sprague-Dawley) average body weight 150 grams. 8 animals per group.

The method consists in the subcutaneous implantation in the dorsal region of 2 sterile cotton pelletts. The pellets employed were 5 mm section cut from dental cotton rolls weighing about 45 mg each. The tested compound dissolved in ethyl alcohol, was absorbed on the pellets before implantation. Fluocinolone acetonide and Dexamethasone-21-acetate was used as comparison products and their activities were conventionally taken equal to 1 for each of the various parameters herein considered. Comparison substance and tested new compounds were absorbed on the pellets at the following scalar dosage per each pellet: 20-2-0.2 mcg/cotton pellet. For the controls the pellets were soakened in the pure solvent (ethyl alcohol) and then dried as usually.

After seven days the animals were sacrificed. The pellets were removed and the exudate weights were recorded as a measure of the granuloma formation. The degree of granuloma inhibition reflects the anti-inflammatory activity of the tested compounds.

In the following Table 1. there are reported the achieved results with regard to the anti-inflammatory activity, the thymolitic activity, and the $LD_{50}$ values:

TABLE 1

| | TOPICAL ADMINISTRATION | | | |
|---|---|---|---|---|
| | Anti-inflammatory activity | | Thymolytic activity | $LD_{50}$ (mg/kg body weight) |
| Product | (*) | (**) | | |
| Dexamethasone 21-acetate | 1 | 1 | 1 | 259 |
| Fluocinolone acetonide | 2 | 2 | 0.83 | 166 |
| Pyr-F-Ac | ≧10 | ≧20 | 0.14 | 721 |
| 16-17 MF-AC | >10 | >20 | 0.02 | >2,000 |
| Pyr Dif-AC | >10 | >20 | 0.52 | 439 |
| 16,17 M Dif-AC | >10 | >20 | 0.26 | 1,120 |

(*)In comparison with Fluocinolone acetonide;
(**)In comparison with Dexamethasone-21-acetate.

From the above data it results that after topical administration the new compounds showed significant anti-inflammatory activity and that they are practically free of thymolytic activity and remarkably less toxic than the comparative substance.

EXPERIMENTAL RESULTS IN HUMAN VOLUNTEERS

Some of the esters have been tested in human volunteers for their vasoconstrictive activity using the McKenzie and Stoughton's test (1) or the Falconi and Rossi's Paper-Patch Test (2) in comparison with a known anti-inflammatory corticosteroid, namely fluocinolone acetonide.

In the first experiment 2 dilutions of 4 esters have been tested on volunteers and 10 dilutions have been applied for each subject.

In the second trial only 16-17 M-Dif-Va which showed the best activity in the first trial has been further tested on 5 subjects using 5 dilutions of the test compound and the same dilutions of triamcinolone acetonide.

The results of the experiments are reported in table 2 and 2a respectively.

| Compound | Dilution | Results (Positive/ No. of subjects) | % Positive |
|---|---|---|---|
| Table | | | |
| Fluocinolone acetonide | $10^4$ | 5/5 | 100 |
| | $10^5$ | 3/5 | 60 |
| 16-17-M-F-Va | $10^4$ | 5/5 | 100 |
| | $10^5$ | 1/5 | 40 |
| 16-17-M-Dif-Va | $10^4$ | 5/5 | 100 |
| | $10^5$ | 2/5 | 40 |
| 16-17-Dif-Bu | $10^4$ | 3/5 | 60 |
| | $10^5$ | 1/5 | 20 |
| 16-17-M-Dif-Piv | $10^4$ | 1/5 | 20 |
| | $10^5$ | 0/5 | 0 |
| Table 2a | | | |
| Triamcinolone acetonide | $10^3$ | 5/5 | 100 |
| | $10^4$ | 5/5 | 100 |
| | $10^5$ | 3/5 | 60 |
| | $10^6$ | 2/5 | 40 |
| 16-17-M-Dif-Va | $10^3$ | 5/5 | 100 |
| | $10^4$ | 4/5 | 80 |
| | $10^5$ | 4/5 | 80 |
| | $10^6$ | 3/5 | 60 |

1. Mc Kenzie, A.W., Stoughton, R.B.: Method for comparing percutaneous absorption of Steroids. Arch. Derm. 86, 608, 1962.
2. Falconi, G., Rossi, G.L.: Paper-Patch Test for evaluating vasoconstrictive activity of Corticosteroids. Arch. Derm. 105, 856, 1972.

From the above table it appears that all the esters tested but 16-17-M-Dif-Piv. has a good vasoconstrictive activity as compared with the test compound beeing active at the higher concentrations used. One of them, 16-17-Dif-Va showed the same potency as fluocinolone acetonide even at the lower concentrations employed in the trials.

What we claim is:

1. A pharmaceutical composition for treating inflammation and rheumatism comprising
a pharmaceutically effective amount of a compound of the formula:

wherein
A is selected from the group consisting of H, Br, and Cl;
X is selected from the group consisting of H, F, or Cl;
Y is selected from the group consisting of β-OH, keto, or Cl;
Z is selected from the group consisting of α-F, β-F, and α-CH₃; and
R is H or an acyl residue selected from the group consisting of a mono- or dicarboxylic organic acid having 2 to 8 carbon atoms, methasulfobenzoic acid, and phosphoric acid, admixed with a pharmaceutically acceptable carrier for topical, intraarticular, and systemic administration.

2. 16α,17α-Pyrazolino-1,4-pregnadiene-6α,9α-difluoro-11β,21-diol-3,20-dione-21-acetate.
3. 16α,17α-Isopyrazolino-1,4-pregnadiene-6α,9α-difluoro-11β,21-diol-3,20-dione-21-acetate.
4. 16α,17α-Pyrazolino-1,4-pregnadiene-11β,21-diol-3,20-dione, 21-acetate.
5. 16α,17α-Isopyrazolino-1,4-pregnadiene-11β,21-diol-3,20-dione-21-acetate.
6. 16α,17α-Isopyrazolino-1,4-pregnadiene-6α,9α-difluoro-11β,21-diol-3,20-dione.
7. 16α,17α-Isopyrazolino-1,4-pregnadiene-6α,9α-difluoro-11β,21-diol-3,20-dione-21-butyrate.
8. 16α,17α-Isopyrazolino-1,4-pregnadiene-6α,9α-difluoro-11β,21-diol-3,20-dione-21-valerate.
9. 16α,17α-Isopyrazolino-1,4-pregnadiene-6α,9α-difluoro-11β,21-diol-3,20-dione-21-pivalate.
10. A pharmaceutical composition for treating inflammation and rheumatism comprising
a pharmaceutically effective amount of a compound of the formula:

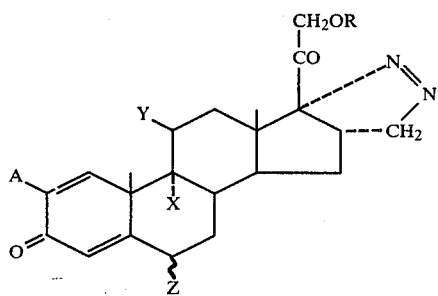

wherein
A is selected from the group consisting of H, Br, and Cl;
X is selected from the group consisting of H, F, or Cl;
Y is selected from the group consisting of β—OH, keto, or Cl;
Z is selected from the group consisting of H, α-F, β-F, and α-CH₃; and
R is H or an acyl residue selected from the group consisting of a mono- or dicarboxylic organic acid having 2 to 8 carbon atoms, methasulfobenzoic acid, and phosphoric acid, admixed with a pharmaceutically acceptable carrier for topical, intraarticular, and systemic administration.

11. A method for treating inflammation in a patient experiencing same comprising
administering to said patient an inflammation reducing quantity of a compound of the formula

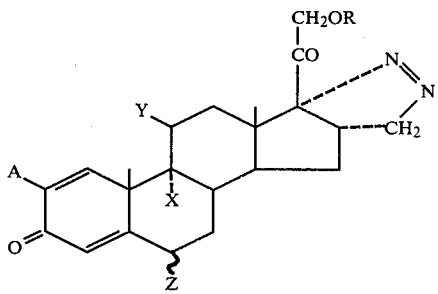

wherein
A is selected from the group consisting of H, Br, and Cl;
X is selected from the group consisting of H, F, or Cl;
Y is selected from the group consisting of β-OH, keto, or Cl;
Z is selected from the group consisting of H, α-F, β-F, and α-CH₃; and
R is H or an acyl residue selected from the group consisting of a mono- or dicarboxyl organic acid having 2 to 8 carbon atoms, methasulfobenzoic acid, and phosphoric acid.

12. A method for treating inflammation in a patient experiencing same comprising
administering to said patient an inflammation reducing quantity of a compound of the formula

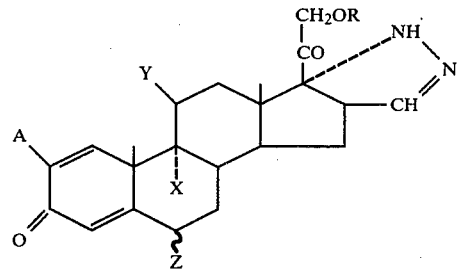

wherein
A is selected from the group consisting of H, Br, and Cl;
X is selected from the group consisting of H, F, or Cl;
Y is selected from the group consisting of β-OH, keto, or Cl;
Z is selected from the group consisting of H, α-F, β-F, and α-CH₃; and
R is H or an acyl residue selected from the group consisting of a mono- or dicarboxyl organic acid having 2 to 8 carbon atoms, methasulfobenzoic acid, and phosphoric acid.

13. A process for the preparation of a 16α,17α-isopyrazolino-1,4-pregnadiene-derivative of structure II:

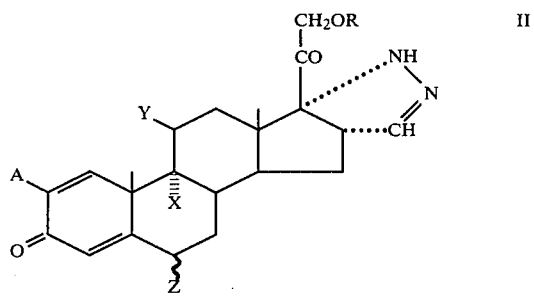

in which X, Y, Z, A and R have the same meaning as in claim 1, which comprises reacting a compound of structure I:

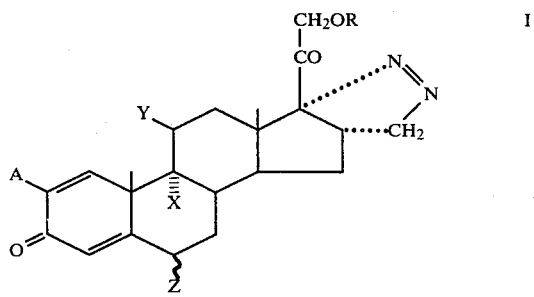

with a strong mineral acid such as hydrochloric acid, hydrobromic acid, hydrofluoric acid, and perchloric acid.

* * * * *